US009930905B2

(12) United States Patent
Petkov et al.

(10) Patent No.: US 9,930,905 B2
(45) Date of Patent: Apr. 3, 2018

(54) **METHOD OF REDUCING *E. COLI* OR *SALMONELLA* CONTAMINATION OF AGRICULTURAL PRODUCTS**

(71) Applicant: Michael Kiril Ltd., Sofia (BG)

(72) Inventors: Kiril Petkov, Sofia (BG); Michael Karsch, New York, NY (US); Petko Petkov, Sofia (BG)

(73) Assignee: Michael Kiril Ltd., Sofia (BG)

( * ) Notice: Subject to any disclaimer, the term of this patent is extended or adjusted under 35 U.S.C. 154(b) by 0 days.

(21) Appl. No.: 14/710,169

(22) Filed: May 12, 2015

(65) Prior Publication Data

US 2015/0342241 A1 Dec. 3, 2015

Related U.S. Application Data

(62) Division of application No. 14/293,522, filed on Jun. 2, 2014.

(51) Int. Cl.
| | |
|---|---|
| *A23L 2/44* | (2006.01) |
| *A23L 3/3571* | (2006.01) |
| *A23L 2/42* | (2006.01) |
| *A01N 63/00* | (2006.01) |
| *A23L 3/36* | (2006.01) |
| *A23B 7/155* | (2006.01) |

(52) U.S. Cl.
CPC ............... *A23L 2/44* (2013.01); *A01N 63/00* (2013.01); *A23B 7/155* (2013.01); *A23L 2/42* (2013.01); *A23L 3/3571* (2013.01); *A23L 3/36* (2013.01); *A23V 2002/00* (2013.01); *A23Y 2220/15* (2013.01)

(58) Field of Classification Search
CPC ..... A23L 2/44; A23L 2/42; A23L 3/36; A23L 3/3571; A23B 7/155
See application file for complete search history.

(56) References Cited

U.S. PATENT DOCUMENTS

| | | | |
|---|---|---|---|
| 4,156,019 A | 5/1979 | Kondratenko et al. | |
| 4,432,998 A | 2/1984 | Peer | |
| 4,842,871 A | 6/1989 | Hill | |
| 5,780,023 A | 7/1998 | McLaughlin et al. | |
| 5,896,811 A * | 4/1999 | Yaow ................ | A23C 9/1226 219/214 |
| 5,922,374 A | 7/1999 | Daury | |
| 7,579,030 B2 | 8/2009 | Domingues et al. | |
| 7,795,000 B2 | 9/2010 | Podtburg et al. | |
| 7,854,950 B2 | 12/2010 | Carroll et al. | |
| 7,901,925 B2 | 3/2011 | Bojrab | |
| 2007/0054008 A1 | 3/2007 | Clayton et al. | |
| 2007/0298019 A1 | 12/2007 | Bojrab | |
| 2008/0181986 A1 | 7/2008 | Terragno et al. | |
| 2010/0086646 A1 | 4/2010 | Francois et al. | |
| 2010/0086968 A1 | 4/2010 | Stahnke et al. | |
| 2012/0003119 A1 | 1/2012 | Powell | |

FOREIGN PATENT DOCUMENTS

| | | |
|---|---|---|
| CN | 101245324 A | 8/2008 |
| WO | WO 2008/112296 A1 | 9/2008 |
| WO | WO 2013/019801 A1 | 2/2013 |

OTHER PUBLICATIONS

Abedi, D. et al., "In vitro anti-bacterial and anti-adherence effects of *Lactobacillus delbrueckii* subsp *bulgaricus* on *Escherichia coli*," *Res. Pharm. Sci.* 8:260-268, School of Pharmacy and Pharmaceutical Sciences, Isfahan University of Medical Sciences and Health Services, Iran (2013).
Boyanova, L., et al., "Anti-*Helicobacter pylori* activity of *Lactobacillus delbrueckii* subsp. *bulgaricus* strains: preliminary report," *Lett. Appl. Microbiol.* 48:579-584, The Society for Applied Microbiology (2009).
Cummings, J.H., et al., "PASSCLAIM—Gut health and immunity," *Eur. J. Nutr.* (Suppl 2)43:II/118-II/173, Steinkopff, Germany (2004).
Das, J.K., et al., "In vitro evaluation of anti-infecetive activity of a *Lactobacillus plantarum* strain against *Salmonella enterica* serovar Enteritidis," *Gut Pathog.* 5, 11 pages, BioMed Central, London (2013).
Fayol-Messaoudi, D., et al., "pH-, Lactic Acid-, and Non-Lactic Acid-Dependent Activities of Probiotic *Lactobacilli* against *Salmonella enterica* Serovar Typhimurium," *Appl. Environ. Microbiol.* 71:6008-6013, American Society for Microbiology (2005).
Howard, M.B. and Hutcheson, S.W., "Growth Dynamics of *Salmonella enterica* Strains on Alfalfa Sprouts and in Waste Seed Irrigation Water," *Appl. Environ. Microbiol.* 69:548-553, American Society for Microbiology (2003).
Hudault, S., et al., "Antagonistic Activity Exerted In Vitro and In Vivo by *Lactobacillus casei* (Strain GG) against *Salmonella typhimurium* C5 Infection," *Appl. Environ. Microbiol.* 63:513-518, American Society for Microbiology (1997).
Reilly, S.S. and Gilliland, S.E., "Inhibition of *Escherichia coli* O157:H7 by *Lactobacillus acidophilus* Isolated from Calves," Research Reports, Department of Animal Science, 5 pages, Oklahoma State University (1996).
Scallan, E., et al., "Foodborne Illness Acquired in the United States—Major Pathogens," *Emerg. Infect. Dis.* 17:7-15, National Centers for Infectious Diseases, Centers for Disease Control and Prevention (2011).

(Continued)

*Primary Examiner* — Felicia C Turner
(74) *Attorney, Agent, or Firm* — Sterne, Kessler, Goldstein & Fox P.L.L.C.

(57) ABSTRACT

The present invention relates to a composition comprising lyophilized *Lactobacilli* and a plant-based food, wherein the composition is substantially free of animal products. The present invention also relates to methods of treating plant-based food by administration of a *Lactobacilli* and a plant medium composition. Methods of using the *Lactobacilli* and plant-based food composition to treat *E. coli* or *Salmonella* infection in an animal in need thereof and methods of using the *Lactobacilli* and plant-based food composition to reduce *E. coli* or *Salmonella* contamination in an agricultural product are also provided.

12 Claims, No Drawings

(56) References Cited

OTHER PUBLICATIONS

Valdez, J.C., et al., "Lactic Acid Bacteria Induce Apoptosis Inhibition in *Salmonella typhimurium* Infected Macrophages," *Food Agric. Immunol.* 13:189-197, Carfax Publishing, United States (2001) (Abstract).

Van Niel, C.W., et al., "Lactobacillus therapy for acute infectious diarrhea in children: a meta-analysis," *Pediatrics* 109:678-684, American Academy of Pediatrics (2002) (Abstract).

Aslim, B., et al., "Factors influencing autoaggregation and aggregation of *Lactobacillus delbrueckii* subsp. *bulgaricus* isolated from handmade yogurt," *Journal of Food Protection* 70(1):223-227, International Association for Food Protection, United States (2007).

Kulp, W.L. and Rettger, L.F., "Comparative Study of *Lactobacillus acidophilus* and *Lactobacillus bulgaricus*," *Journal of Bacteriology* 9(4):357-395, American Society for Microbiology, United States (1924).

Michaylova, M., et al., "Isolation and characterization of *Lactobacullus delbrueckii* ssp. *bulgaricus* and *Streptococcus thermophilus* from plants in Bulgaria," *FEBS Microbiol Lett* 269:160-169, Blackwell Publishing Limited, England (2007).

Zahoor, T., et al., "Viability of *Lactobacillus bulgaricus* as Yoghurt Culture Under Different Preservation Methods," *International Journal of Agriculture and Biology* 5(1):46-48, Friends Science Publishers, Pakistan (2003).

Derwent Abstract for JP 2001-078675, accessed on Mar. 27, 2001, 4 pages.

\* cited by examiner

METHOD OF REDUCING *E. COLI* OR *SALMONELLA* CONTAMINATION OF AGRICULTURAL PRODUCTS

BACKGROUND OF THE INVENTION

Field of the Invention

The present invention relates to a composition comprising lyophilized *Lactobacilli* and a plant-based food, wherein the composition is substantially free of animal products. The present invention also relates to methods of treating plant-based food by administration of a *Lactobacilli* and a plant medium composition. Methods of using the *Lactobacilli* and plant-based food composition to treat *E. coli* or *Salmonella* infection in an animal in need thereof and methods of using the *Lactobacilli* and plant-based food composition to reduce *E. coli* or *Salmonella* contamination in an agricultural product are also provided.

Background Art

Many individuals who are concerned with healthy living focus on eating raw vegan foods. Raw foods are preferred because cooking the food changes the biochemical characteristics of the nutrients in the food and vegan foods are desired because many of these individuals prefer their food not to have any animal products or byproducts. A raw vegan diet, when it is well-balanced, offers positive health benefits to the people who are following it; however, there is a major problem with potential pathogens developing in the food because there are no chemical preservatives present. Usually the manufacturers of raw vegan food depend on refrigeration for food pathogenic bacteria containment; however, low temperatures usually do not eliminate pathogens, rather it only keeps the pathogenic bacteria dormant. Once the food is left at room temperature or it is consumed, the temperature of the food rises creating a positive environment for pathogenic growth. This may lead to food poisoning and other serious illnesses.

In 2006, it was estimated that 31 major pathogens acquired in the United States caused 9.4 million episodes of foodborne illness, 55,961 hospitalizations, and 1,351 deaths. Scallan, E., et al., *Emerging Infectious Diseases* 17:7-15 (2011). Nontyphoidal *Salmonella* accounted for an estimated 1 million episodes of foodborne illnesses, 19,336 hospitalizations, and 378 deaths. And, *Escherichia coli* (*E. coli*) accounted for an estimated 193,800 episodes of foodborne illness, 2,421 hospitalizations, and 20 deaths.

Bacteria from the *Lactobacillus* family is known to have an inhibitory effect on food pathogens; however, most of these bacteria are grown on animal-based medium (such as milk or meat-based medium) since their origin is usually from an animal or human gut. Additionally, the vitality of these bacteria grown using animal-based medium usually decreases significantly in a low temperature environment because their usual environment is the body temperature of their host.

The present invention focuses on identifying specific strains of *Lactobacillus* among the multiple possible strains based on their natural habitat characteristics. The present invention also uses specific strains of *Lactobacillus* as pathogenic inhibitors for vegan foods. Previously, several strains of *Lactobacillus* were used for their known microbial application, namely yogurt production. In choosing a *Lactobacillus* strain to use as a pathogenic inhibitor for vegan foods, three criteria are considered:

Grow well in vegetable or fruit based vegan mediums in a laboratory environment—as it has to be potent and effective in vegan foods.

Survive refrigerated temperatures—as it has to survive the usual refrigeration of vegan foods that is common to manufacturing and storage practices.

Have high inhibitory potency against *E. coli* and *Salmonella* when inserted in contaminated vegan foods.

The bacteria kingdom consists of over 70,000 species and each carry very different characteristics. Probiotics usually involve one of three genuses of bacteria: *Lactobacillus*, *Bifidobacteria*, and *Streptococcus*. In each of these three genuses of bacteria, there are multiple species.

For a bacterial strain to be considered useful in the present invention, the specific bacterial strain should be of plant origin and show vitality in a plant-based environment such as vegan food.

From the known population of good bacteria, *Lactobacillus delbrueckii* subsp. *bulgaricus* was identified as a bacteria for use in the present invention. *Lactobacillus delbrueckii* subsp. *bulgaricus* is found naturally on four different plants in Bulgaria: *Cornus mas* (Cornelian cherry), *Galanthus nivalis* (snowdrop), *Calendula oficinalis* (common marigold), and *Prunus spinosa* (black thorn).

To be useful in the present invention, the specific bacterial strain should survive cold temperatures. In some embodiments, the bacterial strain useful in the present invention survive at a low temperature in its natural environment.

The strain *Lactobacillus delbrueckii* subsp. *bulgaricus* GLB 44 has been identified as bio-identical to bacteria found on *Galanthus nivalis* (snowdrop) in a northern part of Bulgaria in the mountainous region of Staro Selo. The natural habitat for *Galanthus nivalis* is in a mountainous region and the strain is capable of surviving in freezing temperatures because snowdrops grow in early spring and during their growth period, the temperatures fall below freezing.

It is important to note that even though the bacterial strain GLB 44 is of a known variety, it has only been shown to be useful in association with yogurt production in milk environments and it has not heretofore been tested for its survival in different plant-based mediums. Furthermore, it has neither been tested for its ability to survive in artificially refrigerated environments nor has it been tested for its effects on *E. coli* or *Salmonella*. The present invention provides the use of this bacterial strain in compositions comprising *Lactobacilli* and a plant-based food wherein the composition is substantially free of animal products and methods of using these compositions.

BRIEF SUMMARY OF THE INVENTION

In some embodiments, the present invention provides a composition comprising lyophilized *Lactobacilli* and a plant-based food, wherein the composition is substantially free of animal products, and wherein the *Lactobacilli* is *Lactobacillus bulgaricus* strain GLB 44.

In some embodiments, the present invention provides a method of treating plant-based food potentially contaminated with *E. coli* or *Salmonella*, comprising treating the plant-based food with a composition comprising *Lactobacilli* and a plant medium, wherein the *Lactobacilli* is *Lactobacillus bulgaricus* strain GLB 44.

In some embodiments, the present invention provides a method of treating *E. coli* or *Salmonella* infection in an animal in need thereof comprising administering to the animal a composition comprising lyophilized *Lactobacilli* and a plant-based food, wherein the composition is substantially free of animal products, and wherein the *Lactobacilli* is *Lactobacillus bulgaricus* strain GLB 44.

In some embodiments, the plant-based food is a fruit juice or a vegetable juice.

In some embodiments, the plant-based food is a vegetable or fruit sprayed with the *Lactobacilli* or is a vegetable or fruit washed in a solution that contains the *Lactobacilli*.

In some embodiments, the plant-based food is a vegetable or fruit and the *Lactobacilli* is added during culturing.

In some embodiments, the present invention provides a method of reducing *E. coli* or *Salmonella* contamination of an agricultural product, comprising combining with or applying to the agricultural product a composition comprising lyophilized *Lactobacilli*, wherein the composition is substantially free of animal products, and wherein the *Lactobacilli* is *Lactobacillus bulgaricus* strain GLB 44.

In some embodiments, the agricultural product is a fruit juice or a vegetable juice.

In some embodiments, the agricultural product is a vegetable or fruit sprayed with the *Lactobacilli* or is a vegetable or fruit washed with the *Lactobacilli*.

In some embodiments, the composition contains no animal products.

In some embodiments, the vegetable or fruit is sprayed with the composition comprising *Lactobacilli*.

In some embodiments, the vegetable or fruit is washed in a solution that contains the *Lactobacilli*.

In some embodiments, the composition comprising *Lactobacilli* is sprayed in the form of a powder.

In some embodiments, the composition comprising *Lactobacilli* is sprayed in the form of a solution or suspension.

In some embodiments, the plant medium is juice from an acai, an agave, an almond, an aloe, an apple, an apricot, an arugula, an avocado, a beet, a bell pepper, a blackberry, a blue green algae, a blueberry, a carrot, a cayenne, a celery, a chia, a cilantro, a clove, a coconut, a cucumber, a dandelion, a date, a fennel, a garlic, a ginger, a ginkgo, a grapefruit, a guayusa, a hemp, a jalapeno pepper, a kale, a kiwi, a lemon, a lemon grass, a lime, a maca, a mandarin, an onion, an orange, a parsley, a peach, a pear, a pineapple, a raspberry, a spearmint, a spinach, a spirulina, a strawberry, a sweet potato, a tomato, a turmeric root, a watermelon, or a wheatgrass or the plant medium is soya milk, rice milk, almond milk, coffee, flax oil, herbal tea, or maple syrup.

In some embodiments, wherein after combining or applying the composition to the agricultural product, no viable *E. coli* or *Salmonella* remains on the agricultural product.

DETAILED DESCRIPTION OF THE INVENTION

As used herein, the term "substantially free" means that the content is sufficiently low that no appreciable danger to humans will result from contact with the compositions at issue.

As used herein, animal or dairy products or byproducts mean any compound that was produced in or by an animal cell, whether in a living organism or in vitro. Animal products or byproducts include milk, eggs, fish, and crustacean shellfish.

As used herein, the singular terms "a" and "the" are synonymous and used interchangeably with "one or more" and "at least one," unless the language and/or context clearly indicates otherwise.

As used herein, the term "comprising" means including, made up of, and composed of.

All numbers in this description indicating amounts, ratios of materials, physical properties of materials, and/or use are to be understood as modified by the word "about," except as otherwise explicitly indicated.

The term "about" as used herein includes the recited number ±10%. Thus, "about ten" means 9 to 11.

The term "plant-based food" as used herein refers to a material of plant origin that contains essential body nutrients, such as carbohydrates, fats, proteins, vitamins, or minerals, that is ingested and assimilated by an organism to produce energy, stimulate growth, and maintain life. In some embodiments, the plant-based food is a fruit, a vegetable, a grain, or a nut.

As used herein the term "agricultural product" refers to any agricultural commodity or product, whether raw or processed, including any commodity or product derived from livestock, that is marketed for human or livestock consumption. In some embodiments, the agricultural product is a plant-based food, a fiber, a fuel, a flower, an ornamental plant, or a nursery plant. In some embodiments, the agricultural product is a plant-based food.

The term "package" as used herein refers to any type of container, box, carton, bag, or bin that can be filled with plant-based foods. A package is designed to contain a relatively large quantity of plant-based foods.

The genus *Lactobacillus* contains over 180 species. In some embodiments, the *Lactobacilli* are of the species *L. acidophilus, L. brevis, L. buchneri, L. casei, L. curvatus, L. delbrueckii, L. fermentum, L. helveticus, L. plantarum, L. reuteri, L. sakei*, or *L. salivarius*. In some embodiments, the *Lactobacilli* are from the species *L. delbrueckii*. In some embodiments, the *Lactobacilli* is *Lactobacilli delbrueckii bulgaris, Lactobacilli delbrueckii lactis, Lactobacilli delbrueckii delbrueckii*, or *Lactobacilli delbrueckii indicus*. In some embodiments, the *Lactobacilli* is *Lactobacilli delbrueckii bulgaris*. In some embodiments, the *Lactobacilli* is *Lactobacillus delbrueckii bulgaricus* strain GLB 44.

*Lactobacillus delbrueckii* subsp. *bulgaricus* GLB 44, was deposited with the National Bank for Industrial Microorganisms and Cell Cultures located at 1756 Sofia, 49 St Kilment Ohridski blvd., bild. 3, Sofia, Bulgaria on Apr. 17, 2014, under NBIMCC Accession Number 8814.

The present invention is based on the finding that animal products are not required as ingredients in media for the growth of *Lactobacilli*, and therefore, plant products can replace the animal products that are typically employed in such media for the growth of *Lactobacilli*. One commonly used growth medium for the production of *Lactobacillus bulgaricus* is *Lactobacillus bulgaricus* agar base which contains casein enzymic hydrolysate (a protein found in animal milk) and beef extract. Replacing the animal components with vegetable-based products reduces the potential for contamination by biological molecules such as proteins and viruses that exist in animals.

Additionally, a composition comprising Lactobaccilli grown in a plant medium can be used to replace harsh chemicals used to treat food products prior to packaging. For example, baby carrots are currently treated with a chlorine bath before packaging to limit the risk of food-borne illnesses such as *E. coli*. Use of harsh chemicals can result in degradation of the nutritional value of the food products. Replacing the harsh chemicals with a composition of the present invention can allow for retention of valuable nutrients.

In some embodiments, the *Lactobacilli* is grown in a plant medium. In some embodiments, the plant medium comprises a vegetable, a fruit, a nut, or a grain. In some embodiments, the plant medium comprises the juice of a vegetable, a fruit, a nut, or a grain. In some embodiments, the plant medium comprises carrot juice or soya milk.

In some embodiments, the media for growth of *Lactobacilli* contains animal products comprising no more than 10%, no more than 9%, no more than 8%, no more than 7%, no more than 6%, no more than 5%, no more than 4%, no more than 3%, no more than 2%, no more than 1%, no more than 0.9%, no more than 0.8%, no more than 0.7%, no more than 0.6%, no more than 0.5%, no more than 0.4%, no more than 0.3%, no more than 0.2%, or no more than 0.1% of the total weight of the media. In some embodiments, the growth media is substantially free of animal products. In some embodiments, the growth media contains no animal products. In some embodiments, the growth media contains no more than $10^9$ live CFU/gram of animal products.

In some embodiments, the present invention provides a composition comprising *Lactobacilli* and a plant-based food. In some embodiments, the present invention provides a composition comprising *Lactobacilli* and a plant medium.

In some embodiments, the composition is a liquid, a solid, or a semi-solid. In some embodiments, the composition is lyophilized prior to packaging. In some embodiments, the composition is in the form of a solution, a suspension, an emulsion, a powder, a granule, a tablet, a pellet, a multiparticulate, or a capsule. In some embodiments, the composition is in the form of a powder. In some embodiments, the composition is in the form of a solution or a suspension.

In some embodiments, the composition comprising *Lactobacilli* contains animal products comprising no more than 10%, no more than 9%, no more than 8%, no more than 7%, no more than 6%, no more than 5%, no more than 4%, no more than 3%, no more than 2%, no more than 1%, no more than 0.9%, no more than 0.8%, no more than 0.7%, no more than 0.6%, no more than 0.5%, no more than 0.4%, no more than 0.3%, no more than 0.2%, or no more than 0.1% of the total weight of the media. In some embodiments, the composition comprising *Lactobacilli* is substantially free of animal products. In some embodiments, the composition comprising *Lactobacilli* contains no animal products. In some embodiments, the compositions contains no more than $10^9$ live CFU/gram of animal products.

If the composition is a liquid, the concentration of *Lactobacilli* can be an estimate of colony-forming units per milliliter (CFU/mL). In some embodiments, the concentration of *Lactobacilli* in the composition is from 0.5 million to 1 billion CFU/mL, 0.5 million to 500 million CFU/mL, 0.5 million to 400 million CFU/mL, 0.5 million to 300 million CFU/mL, 0.5 million to 200 million CFU/mL, 0.5 million to 150 million CFU/mL, 0.5 million to 125 million CFU/mL, 0.5 million to 100 million CFU/mL, 0.5 million to 75 million CFU/mL, 0.5 million to 50 million CFU/mL, 0.5 million to 10 million CFU/mL, 0.5 million to 5 million CFU/mL, 0.5 million to 1 million CFU/mL, 1 million to 1 billion CFU/mL, 1 million to 500 million CFU/mL, 1 million to 400 million CFU/mL, 1 million to 300 million CFU/mL, 1 million to 200 million CFU/mL, 1 million to 150 million CFU/mL, 1 million to 125 million CFU/mL, 1 million to 100 million CFU/mL, 1 million to 75 million CFU/mL, 1 million to 50 million CFU/mL, 1 million to 10 million CFU/mL, 1 million to 5 million CFU/mL, 5 million to 1 billion CFU/mL, 5 million to 500 million CFU/mL, 5 million to 400 million CFU/mL, 5 million to 300 million CFU/mL, 5 million to 200 million CFU/mL, 5 million to 150 million CFU/mL, 5 million to 125 million CFU/mL, 5 million to 100 million CFU/mL, 5 million to 75 million CFU/mL, 5 million to 50 million CFU/mL, 5 million to 10 million CFU/mL, 10 million to 1 billion CFU/mL, 10 million to 500 million CFU/mL, 10 million to 400 million CFU/mL, 10 million to 300 million CFU/mL, 10 million to 200 million CFU/mL, 10 million to 150 million CFU/mL, 10 million to 125 million CFU/mL, 10 million to 100 million CFU/mL, 10 million to 75 million CFU/mL, 10 million to 50 million CFU/mL, 50 million to 1 billion CFU/mL, 50 million to 500 million CFU/mL, 50 million to 400 million CFU/mL, 50 million to 300 million CFU/mL, 50 million to 200 million CFU/mL, 50 million to 150 million CFU/mL, 50 million to 125 million CFU/mL, 50 million to 100 million CFU/mL, 50 million to 75 million CFU/mL, 100 million to 1 billion CFU/mL, 100 million to 500 million CFU/mL, 100 million to 400 million CFU/mL, 100 million to 300 million CFU/mL, 100 million to 200 million CFU/mL, 100 million to 150 million CFU/mL, 100 million to 125 million CFU/mL, 125 million to 1 billion CFU/mL, 125 million to 500 million CFU/mL, 125 million to 400 million CFU/mL, 125 million to 300 million CFU/mL, 125 million to 200 million CFU/mL, 125 million to 150 million CFU/mL, 150 million to 1 billion CFU/mL, 150 million to 500 million CFU/mL, 150 million to 400 million CFU/mL, 150 million to 300 million CFU/mL, 150 million to 200 million CFU/mL, 200 million to 1 billion CFU/mL, 200 million to 500 million CFU/mL, 200 million to 400 million CFU/mL, 200 million to 300 million CFU/mL, 300 million to 1 billion CFU/mL, 300 million to 500 million CFU/mL, 300 million to 400 million CFU/mL, 400 million to 1 billion CFU/mL, 400 million to 500 million CFU/mL, or 500 million to 1 billion CFU/mL.

If the composition is a solid, the concentration of *Lactobacilli* can be an estimate of colony-forming units per gram (CFU/g). In some embodiments, the concentration of *Lactobacilli* in the composition is from 0.5 million to 1 billion CFU/g, 0.5 million to 500 million CFU/g, 0.5 million to 400 million CFU/g, 0.5 million to 300 million CFU/g, 0.5 million to 200 million CFU/g, 0.5 million to 150 million CFU/g, 0.5 million to 125 million CFU/g, 0.5 million to 100 million CFU/g, 0.5 million to 75 million CFU/g, 0.5 million to 50 million CFU/g, 0.5 million to 10 million CFU/g, 0.5 million to 5 million CFU/g, 0.5 million to 1 million CFU/g, 1 million to 1 billion CFU/g, 1 million to 500 million CFU/g, 1 million to 400 million CFU/g, 1 million to 300 million CFU/g, 1 million to 200 million CFU/g, 1 million to 150 million CFU/g, 1 million to 125 million CFU/g, 1 million to 100 million CFU/g, 1 million to 75 million CFU/g, 1 million to 50 million CFU/g, 1 million to 10 million CFU/g, 1 million to 5 million CFU/g, 5 million to 1 billion CFU/g, 5 million to 500 million CFU/g, 5 million to 400 million CFU/g, 5 million to 300 million CFU/g, 5 million to 200 million CFU/g, 5 million to 150 million CFU/g, 5 million to 125 million CFU/g, 5 million to 100 million CFU/g, 5 million to 75 million CFU/g, 5 million to 50 million CFU/g, 5 million to 10 million CFU/g, 10 million to 1 billion CFU/g, 10 million to 500 million CFU/g, 10 million to 400 million CFU/g, 10 million to 300 million CFU/g, 10 million to 200 million CFU/g, 10 million to 150 million CFU/g, 10 million to 125 million CFU/g, 10 million to 100 million CFU/g, 10 million to 75 million CFU/g, 10 million to 50 million CFU/g, 50 million to 1 billion CFU/g, 50 million to 500 million CFU/g, 50 million to 400 million CFU/g, 50 million to 300 million CFU/g, 50 million to 200 million CFU/g, 50 million to 150 million CFU/g, 50 million to 125 million CFU/g, 50 million to 100 million CFU/g, 50 million to 75 million CFU/g, 100 million to 1 billion CFU/g, 100 million to 500 million CFU/g, 100 million to 400 million CFU/g, 100 million to 300 million CFU/g, 100 million to 200 million CFU/g, 100 million to 150 million CFU/g, 100 million to 125 million CFU/g, 125 million to 1 billion CFU/g, 125 million to 500 million CFU/g, 125 million to 400 million CFU/g, 125 million to 300 million CFU/g, 125 million to 200 million CFU/g, 125 million to 150 million CFU/g, 150 million to 1 billion CFU/g, 150 million to 500 million CFU/g, 150 million to 400 million CFU/g, 150 million to 300 million CFU/g, 150 million to 200 million CFU/g, 200 million to 1 billion CFU/g, 200 million to 500 million CFU/g, 200 million to 400 million CFU/g, 200 million to 300 million CFU/g, 300 million to 1 billion CFU/g, 300 million to 500 million CFU/g, 300 million to 400 million CFU/g, 400 million to 1 billion CFU/g, 400 million to 500 million CFU/g, or 500 million to 1 billion CFU/g.

In some embodiments, the composition is administered to a plant-based food. In some embodiments, the composition is administered to an agricultural product. In some embodiments, the composition is administered to an animal in need thereof. In some embodiments, the composition is administered by low pressure spraying, high pressure spraying, brushing, misting, vaporizing, volatilizing, fogging, fumigating, immersing, injecting, vapor treating, pressure treating, drenching, drip irrigating, atomizing, broadcasting, or foaming. In some embodiments, the composition is administered using an emulsion, a solution, a concentrate, a cover, a vapor, a capsule, or a microcapsule. In some embodiments, the composition is administered using a fogger, a sprayer, a diffusor, a box, an envelope, a paper, a tunnel, a postharvest room, a container, a cooling room, or a refrigerator. In some embodiments, the composition is administered by spraying. In some embodiments, the composition is administered as a solution. In some embodiments, the composition is administered as an suspension. In some embodiments, the composition is administered as a powder.

In some embodiments, the composition is administered as a solution or a spray. In some embodiments, the solution or the spray further comprises a solvent. In some embodiments, the solvent is water.

In some embodiments, the composition is administered for 1 second to 14 days, 1 second to 7 days, 1 second to 1 day, 1 second to 16 hours, 1 second to 8 hours, 1 second to 1 hour, 1 second to 30 minutes, 1 second to 10 minutes, 1 second to 1 minute, 1 second to 30 seconds, 30 seconds to 14 days, 30 seconds to 7 days, 30 seconds to 1 day, 30 seconds to 16 hours, 30 seconds to 8 hours, 30 seconds to 1 hour, 30 seconds to 30 minutes, 30 seconds to 10 minutes, 30 seconds to 1 minute, 1 minute to 14 days, 1 minute to 7 days, 1 minute to 1 day, 1 minute to 16 hours, 1 minute to 8 hours, 1 minute to 1 hour, 1 minute to 30 minutes, 1 minute to 10 minutes, 10 minutes to 14 days, 10 minutes to 7 days, 10 minutes to 1 day, 10 minutes to 16 hours, 10 minutes to 8 hours, 10 minutes to 1 hour, 10 minutes to 30 minutes, 30 minutes to 14 days, 30 minutes to 7 days, 30 minutes to 1 day, 30 minutes to 16 hours, 30 minutes to 8 hours, 30 minutes to 1 hour, 1 hour to 14 days, 1 hour to 7 days, 1 hour to 1 day, 1 hour to 16 hours, 1 hour to 8 hours, 8 hours to 14 days, 8 hours to 7 days, 8 hours to 1 day, 8 hours to 16 hours, 16 hours to 14 days, 16 hours to 7 days, 16 hours to 1 day, 1 day to 7 days, 1 day to 14 days, or 7 days to 14 days.

In some embodiments, the composition comprises one or more plant-based foods. In some embodiments, the composition is applied to one or more plant-based foods. In some embodiments, the composition is applied to a package of plant-based foods. In some embodiments, the plant-based food is a fruit, a vegetable, a grain, a nut, or combinations thereof.

In some embodiments, the plant-based food is a fruit. In some embodiments, the plant-based food is one or more fruits. In some embodiments, the plant-based food is a package of fruit. In some embodiments, plant-based food is fruit juice.

In some embodiments, the plant medium comprises a fruit.

In some embodiments, the fruit is an apple, an apricot, an avocado, a banana, a breadfruit, a bilberry, a blackberry, a blackcurrant, a blue green algae, a blueberry, a boysenberry, a currant, a cherry, a cherimoya, a chili, a cloudberry, a coconut, a damson, a date, a dragonfruit, a durian, an elderberry, a feijoa, a fig, a gooseberry, a grape, a grapefruit, a guava, a huckleberry, a jackfruit, a jettamelon, a jambul, a jujube, a kiwi fruit, a kumquat, a lemon, a lime, a loquat, a lychee, a mango, a melon, a canary melon, a cantaloupe, a honeydew, a watermelon, a rock melon, a nectarine, a nut, an orange, a clementine, a mandarine, a tangerine, a papaya, a peach, a pepper, a pear, a persimmon, a tomatillo, a plum, a pineapple, a pomegranate, a pomelo, a mangosteen, a quince, a raspberry, a rambutan, a redcurrant, a salal berry, a satsuma, a star fruit, a strawberry, a tamarillo, a tomato, or an ugli fruit. In some embodiments, the plant-based food is an orange or an apple. In some embodiments, the plant-based food is orange juice or apple juice.

In some embodiments, the plant-based food is a vegetable. In some embodiments, the plant-based food is one or more vegetables. In some embodiments, the plant-based food is a package of vegetables. In some embodiments, plant-based food is vegetable juice.

In some embodiments, the plant medium comprises a vegetable. In some embodiments, the plant medium comprises vegetable juice. In some embodiments, the plant medium is soya milk or carrot juice.

In some embodiments, the juice is pasteurized, fresh, or Healthcare Professional Profile (HPP) tested.

In some embodiments, the juice does not contain significant traces of chlorine, pesticides, or other chemical bacterial inhibitors.

In some embodiments, the temperature of the juice is above 32° F. (0° C.) when the *Lactobacilli* is added to the juice. In some embodiments, the temperature of the juice is below 113° F. (45° C.) when the *Lactobacilli* is added to the juice. In the some embodiments, the temperature of the juice is between 32° F. (0° C.) and 113° F. (45° C.) when the *Lactobacilli* is added to the juice.

In some embodiments, the acidity of the juice is between a pH of 3.5 to 4.0. In some embodiments, the acidity of juice is at a pH less than 8.0.

In some embodiments, the vegetable is an artichoke, an arugula, an asparagus, an eggplant (aubergine), an avocado, an amaranth, an alfalfa sprout, an azuki bean, a bean sprout, a black bean, a black-eyed pea, a borlotti bean, a chickpea, a green bean, a kidney bean, a lentil, a lima bean, a mung bean, a navy bean, a pinto bean, a runner bean, a soybean, a pea, a bok Choy, a breadfruit, a broccoflower, a broccoli, a brussel sprout, a cabbage, a calabrese, a carrot, a cauliflower, a celery, a chard, a collard green, a corn, an endive, a fiddlehead, a frisee, an anise, a basil, a coriander, a chamomile, a dill, a fennel, a lavender, a lemon grass, a marjoram, an oregano, a parsley, a rosemary, a sage, a thyme, a kale, a kohlrabi, a lettuce, a mushroom, a mustard green, a nettle, a spinach, an okra, a chive, a garlic, a leek, an onion, a shallot, a scallion, a bell pepper, a green pepper, a chili pepper, a jalapeno pepper, a habanero pepper, a paprika pepper, a tabasco pepper, a cayenne pepper, a radicchio, a rhubarb, a beetroot, a celeriac, a daikon, a ginger, a parsnip, a rutabaga, a turnip, a radish, a horseradish, a salsify, a skirret, an artichoke, a topinambur, an acorn squash, a butternut squash, a banana squash, a zucchini, a cucumber, a delicata, a gem squash, a hubbard squash, a pumpkin, a spaghetti squash, a tat soi, a jicama, a Jerusalem artichoke, a potato, a sweet potato, a taro, a yam, a water chestnut, or a watercress. In some embodiments, the vegetable is a carrot, a kale, a beet, or a cucumber. In some embodiments, the vegetable is carrot juice, kale juice, beet juice, or cucumber juice.

In some embodiments, the plant-based food is a grain. In some embodiments, the plant-based food is one or more grains. In some embodiments, the plant-based food is a package of grain.

In some embodiments, the plant medium comprises a grain.

In some embodiments, the grain is amaranth, barley, hulled barley, Scotch barley, pearl barley, barley flakes, barley grits, buckwheat, buckwheat groats, roasted buckwheat, buckwheat grits, corn, hominy, popcorn, millet, oats, oat groats, rolled oats, steel cut oats, quick cooking oats, instant oats, oat bran, quinoa, rice, rye, rye berries, cracked rye, rye flakes, sorghum, spelt, spelt berries, spelt flakes, teff, triticale, triticale berries, triticale flakes, wheat, wheat berries, bulgur wheat, cracked wheat, farina, semolina, wheat bran, wheat flakes, or wild rice.

In some embodiments, the plant-based food is a nut. In some embodiments, the plant-based food is one or more nuts. In some embodiments, the plant-based food is a package of nuts.

In some embodiments, the plant medium comprises a nut.

In some embodiments, the nut is an acorn, an almond, a Brazil nut, a candlenut, a cashew, a chestnut, a coconut, a hazelnut, a filbert, a kola nut, a macadamia nut, a peanut, a pecan, a pili nut, a pine nut, a pistachio nut, a soynut, a walnut, a black walnut, a butternut, or a heartnut.

In some embodiments, the plant-based food is an acai, an agave, an almond, an aloe, an apple, an apricot, an arugula, an avocado, a beet, a bell pepper, a blackberry, a blue green algae, a blueberry, a carrot, a cayenne, a celery, a chia, a chlorophyll, a cilantro, a clove, a coconut, a coffee, a cucumber, a dandelion, a date, a fennel, a flax oil, a garlic, a ginger, a ginkgo, a grapefruit, a guayusa, a hemp, a hempseed, a hibiscus tea, a jalapeno pepper, a kale, a kiwi, a lemon, a lemon grass, a lime, a maca, a mandarin, a maple syrup, an onion, an orange, a parsley, a peach, a pear, a pineapple, a raspberry, a spearmint, a spinach, a spirulina, a strawberry, a sweet potato, a tahini, a tomato, a turmeric root, a watermelon, or a wheatgrass. In some embodiments, the plant-based food is juice from an acai, an agave, an almond, an aloe, an apple, an apricot, an arugula, an avocado, a beet, a bell pepper, a blackberry, a blue green algae, a blueberry, a carrot, a cayenne, a celery, a chia, a cilantro, a clove, a coconut, a cucumber, a dandelion, a date, a fennel, a garlic, a ginger, a ginkgo, a grapefruit, a guayusa, a hemp, a jalapeno pepper, a kale, a kiwi, a lemon, a lemon grass, a lime, a maca, a mandarin, an onion, an orange, a parsley, a peach, a pear, a pineapple, a raspberry, a spearmint, a spinach, a spirulina, a strawberry, a sweet potato, a tomato, a turmeric root, a watermelon, or a wheatgrass or the plant medium is soya milk, rice milk, almond milk, coffee, flax oil, herbal tea, or maple syrup In some embodiments, the present invention provides a method of treating a pathogenic infection in an animal in need thereof comprising administering to the animal a composition comprising lyophilized *Lactobacilli* and a plant-based food. In some embodiments, the *Lactobacilli* is *Lactobacilli bulgaricus*. In some embodiments, the *Lactobacilli* is *Lactobacilli bulgaricus* strain GLB 44.

In some embodiments, the composition contains no animal products.

In some embodiments, the plant-based food is a fruit juice or a vegetable juice.

In some embodiments, the plant-based food is a vegetable or fruit sprayed with the *Lactobacilli*, is a vegetable or fruit wherein the *Lactobacilli* is added during culturing, or is a vegetable or fruit washed in a solution that contains the *Lactobacilli*.

In some embodiments, the vegetable or fruit is sprayed with the *Lactobacilli*.

In some embodiments, the vegetable or fruit is washed in a solution that contains the *Lactobacilli*.

In some embodiments, the *Lactobacilli* is sprayed in the form of a powder.

In some embodiments, the *Lactobacilli* is sprayed in the form of a solution or suspension.

In some embodiments, the plant medium is carrot juice or soya milk.

As used herein, the term "animal" includes all members of the animal kingdom including humans. In some embodiments, the animal is a mammal. In some embodiments, the animal is a human.

As used herein, "treatment" is an approach for obtaining beneficial results, including clinical results. Beneficial or desired results can include, but are not limited to, alleviation or amelioration of one or more symptoms of the condition, diminishment of the extent of the condition, or stabilization of the state of the condition.

In some embodiments, the pathogen is a *Salmonella Enterica* serotype. In some embodiments, the pathogen is *Salmonella typhimurium, Salmonella enteritidis, Salmonella newport, Salmonella hadar, Salmonella oranienburg, Salmonella javiana, Salmonella saintpaul, Salmonella muenchen, Salmonella agona, Salmonella I monophasic, Salmonella montevideo,* or *Salmonella paratyphi*. In some embodiments, the pathogen is *Salmonella typhimurium*. In some embodiments, the pathogen is *Salmonella enteritidis*.

In some embodiments, the pathogen is *Bacillus cereus, Campylobacter jejuni, Clostridium botulinum, Clostridium perfringens, Cryptosporidium parvum, Escherichia coli, Giardia lamblia*, Hepatitis A, *Listeria monocytogenes*, Norwalk virus, *Staphylococcus*, Shingella, *Toxoplasma gondii, Vibrio,* or Yersiniosis. In some embodiments, the pathogen is *Escherichia coli*.

In some embodiments, the composition is administered in the form of a solution, a suspension, an emulsion, a powder, a granule, a tablet, a pellet, a multi-particulate, or a capsule. In some embodiments, the composition is in administered in the form of a solution which is sprayed onto a vegetable, fruit, nut, or grain. In some embodiments, the composition is administered in the form of a powder which is dusted onto a vegetable, fruit, nut, or grain. In some embodiments, the composition is administered in the form of a solution or suspension.

In some embodiments, the plant-based food resists disease by pathogenic infection after application for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least two months, at least three months, at least four months, at least five months, at least six months, at least seven months, at least eight months, at least nine months, at least ten months, at least eleven months, or at least one year.

In some embodiments, after combining or applying the composition to the agricultural product, no viable *E. coli* or *Salmonella* remains on the agricultural product.

In some embodiments, the plant package is a bag, a crate, a hamper, a basket, a carton, a bulk bin, a palletized container, a flat, a fiberboard container, a mesh bag, a plastic bag, a paper bag, a rigid plastic container, a plastic tray, or a clamshell.

In some embodiments, the plant package contains one or more plants. In some embodiments, the number of plants in the plant package is at least 1, at least 2, at least 5, at least 8, at least 10, at least 25, at least 50, at least 75, at least 100, at least 125, at least 150, at least 175, at least 200, at least 225, at least 250, at least 275, at least 300, at least 400, at least 500, at least 600, at least 700, at least 800, at least 900, or at least 1000.

In some embodiments, the plant or plant package is stored, after application of the composition, at a temperature less than 1° C., less than 2° C., less than 3° C., less than 4° C., less than 5° C., less than 6° C., less than 7° C., less than 8° C., less than 9° C., less than 10° C., less than 11° C., less than 12° C., less than 13° C., less than 14° C., less than 15° C., less than 16° C., less than 17° C., less than 18° C., less than 19° C., less than 20° C., less than 21° C., less than 22° C., less than 23° C., less than 24° C., less than 25° C., or less than 26° C.

In some embodiments, the plant or plant package is stored, after application of the composition, for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least two months, at least three months, at least four months, at least five months, at least six months, at least seven months, at least eight months, at least nine months, at least ten months, at least eleven months, or at least one year.

In some embodiments, the plant or plant package is stored in a refrigerated environment at a temperature of between 35° F. and 50° F., between 35° F. and 45° F., between 35° F. and 40° F., between 40° F. and 50° F., between 40° F. and 45° F., or between 45° F. and 50° F. In some embodiments, the plant-based food is stored in a refrigerated environment with a temperature of between 35° F. and 45° F.

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

EXAMPLES

Example 1

Determination of Survival of GLB 44 in Vegetable and Fruit Foods Sample Solution Preparation 1 gram of *Lactobacillus delbrueckii* subsp. *bulgaricus* (GLB 44) with a concentration $1 \times 10^9$ colony-forming units per gram (CFU/g) is inserted into 1 liter of each of the following 7 fruit and vegetable juices: orange juice, apple juice, carrot juice, beet juice, kale juice, pineapple juice, and cucumber juice.

GLB 44 inserted juice samples are placed in a refrigerated environment at 40° F. 10 mL samples are collected from each of the juices at 24 hours and 48 hours after the juices were placed in the refrigerated environment.

Control Solution Preparation 1 gram of GLB 44 with a concentration $1 \times 10^9$ CFU/g is inserted into 1 liter of sterile milk.

Growth Medium Solution Preparation 10 mL samples from all seven of the juice solutions and the control solution are added to individual 100 mL milk mediums that are stabilized at pH of 6.3 with a temperature of 98.6° F.

Measuring the Vitality of GLB 44 Via pH Measurements

The pH of each of the growth medium solutions is measured at 0 hours, 12 hours, 15 hours, and 16 hours after the juice sample and the control sample was inserted into the milk mediums. The faster the pH of the growth solutions falls, the more vital is the GLB 44 to that solution.

Results

The results of the pH measurements of the growth medium solutions containing juice samples and the control sample are shown in Table 1. As shown in Table 1, GLB 44 survived very well in vegan mediums of fruit and vegetable juices that had been refrigerated for 24 hours and 48 hours. And, GLB 44 showed a higher activity than the control sample, which was not exposed to refrigerated temperatures, in the following refrigerated juices: cucumber, beet, carrot, and kale. In the apple and orange juice samples, GLB 44 also showed good vitality but slightly less than the control sample. Therefore, GLB 44 was well tolerated in vegan environments and withstood refrigerated temperatures. This corresponds to the *bulgaricus* strain which is mainly derived from the leaves of a snowdrop flower, and this strain has shown to be suitable for insertion in vegan foods that are stored in a refrigerated temperature.

TABLE 1

| | pH | | | |
|---|---|---|---|---|
| Sample | 0 h | 12 h | 15 h | 16 h |
| Control GLB 44 | 6.30 | 4.36 | 4.24 | 4.13 |
| Orange (24 hours) | 6.30 | 5.74 | 4.90 | 4.68 |
| Orange (48 hours) | 6.30 | 5.95 | 5.12 | 4.80 |
| Apple (24 hours) | 6.30 | 5.09 | 4.56 | 4.44 |
| Apple (48 hours) | 6.30 | 5.15 | 4.62 | 4.54 |
| Carrot (24 hours) | 6.30 | 4.24 | 4.13 | 4.06 |
| Carrot (48 hours) | 6.30 | 4.25 | 4.12 | 4.10 |
| Kale (24 hours) | 6.30 | 4.20 | 4.10 | 4.05 |
| Kale (48 hours) | 6.30 | 4.21 | 4.12 | 4.06 |
| Beet (24 hours) | 6.30 | 4.30 | 4.19 | 4.12 |
| Beet (48 hours) | 6.30 | 4.37 | 4.25 | 4.22 |
| Cucumber (24 hours) | 6.30 | 4.27 | 4.16 | 4.09 |
| Cucumber (48 hours) | 6.30 | 4.28 | 4.15 | 4.13 |

Example 2

Pathogen Inhibitory Effect of GLB 44 Against *E. coli* and *Salmonella*

Test Goal

This example was designed to determine whether *Lactobacillus delbrueckii* subsp. *bulgaricus* (GLB 44) inhibits the presence of pathogens and prevents food poisoning in healthy people who have consumed vegetable and fruit juice containing GLB 44 together with *Escherichia coli* (*E. coli*) or *Salmonella Enterica* Serotype *typhimurium* (*S. typhimurium*).

Test Materials

Lyophilized *Lactobacillus delbrueckii* subsp. *bulgaricus* GLB 44 powder (concentration=1×10$^9$ CFU/g);

2000 mL of organic carrot juice; and

Nutrient Agar powder (CM0003, Oxoid Limited, Basingstoke, Dartford).

Bacterial Culture Preparation

Prepare and let sit overnight a culture of *E. coli* and *S. typhimurium* at 98.6° F. (37° C.) in Brain Hart Infusion or Nutrient Broth. The observed count of live bacteria in the culture is approximately 0.6 to 0.8×10$^9$ CFU/mL.

Performed 10 fold dilutions in saline from 10$^{-1}$ to 10$^{-6}$ (for example, 0.5 mL of the culture in 4.5 mL of saline) using a separate tip for each dilution.

Plate 100 µL of 10$^{-4}$, 10$^{-5}$, and 10$^{-6}$ on nutrient agar and spread the samples on the agar surface. Count the number of bacterial colonies the next day. Depending of the broth media the number of live bacteria in 10$^{-6}$ is approximately 1,000 CFU/mL.

E. Coli Test Methodology

Control Sample: 50 mL of raw carrot juice is infected with 1,000±100 live cells of *E. coli*. 5 identical control samples of 50 mL are prepared. To determine the exact number of live cells in the initial control sample, the *E. coli* solution concentration of live bacterial cells measured in colony forming units (CFU) is pre-counted on Nutrient Agar. Appropriate dilutions are made to transfer approximately 1,000 live CFU into each 50 mL control sample of carrot juice.

Test Samples: 50 mL of raw carrot juice containing 50 mg of lyophilized *Lactobacillus delbrueckii* subsp. *bulgaricus* (GLB 44) powder (powder concentration is 1×10$^9$ CFU/g) is contaminated with 1,000±100 live cells of *E. coli*. 5 identical test samples of 50 mL are prepared. The same method is used as in the control sample to ensure that 1,000±100 live CFU is placed in each 50 ml test sample.

To transfer the correct amount of GLB 44 powder and ensure that it is well mixed, the following method is used: Place 1 g of GLB 44 in 9 mL of sterile water at room temperature. Mix this solution for 3 to 5 minutes to ensure that it is homogeneous. Pipette 0.5 mL of the mixture and transfer to each 50 mL test sample.

The five test samples and the five control samples are placed in a refrigerated environment for 24 hours at 43° F. This replicates the manufacturing process for juice in which the vegetables are not cleaned properly and are contaminated with trace amounts of *E. coli*. In this process, the juice is produced and then cooled down for at least 24 hours prior to reaching the hands of the consumer.

After 24 hours at 43° F., the samples are placed in a chamber at a temperature of 98.6° F. for 48 hours. According to Department of Cell Biology and Molecular Genetics, University of Maryland, College Park, Md., the pathogenic growth maximum value is achieved after 48 h. M. B. Howard and S. W. Hutcheson, *Applied and Environmental Microbiology* 69:548-553 (2003). Also according to the European Journal of Nutrition, the mean Transit Time for healthy individuals is 62 hours. Cumming, J. H., et al., *Eur. J. Nutr.* 43 (Suppl. 2):118-173 (2004). Since the transit time on average is longer than maximum pathogenic count value, it is therefore reasonable to leave the samples at 98.6° F. for 48 hours prior to making the bacterial count. The importance of this step is to see how both bacteria grow, and to determine whether GLB 44 has a pathogenic inhibitory effect once both bacteria are put into a body temperature environment, after 24 hours at refrigerating temperature.

After both periods have elapsed, each of the control samples and test samples are grown out in Nutrient Agar (CM0003, Oxoid Limited, Basingstoke, Dartford) on which the GLB 44 does not grow but *E. coli* grows. The count of live bacteria is estimated by plating 10 fold dilutions in saline on Nutrient Agar and counting the colonies (CFU) in each dilution.

The same procedures are repeated for higher contaminant concentration of the *E. coli*, namely:

10,000 CFU/50 mL (200 CFU/mL)

100,000 CFU/50 mL (2,000 CFU/mL)

1,000,000 CFU/50 mL (20,000 CFU/mL)

10,000,000 CFU/50 mL (200,000 CFU/mL)

Salmonella typhimurium Test Methodology

Control Sample: 50 mL of raw carrot juice is infected with 1,000±100 live cells of *E. coli*. 5 identical control samples of 50 mL are prepared. To determine the exact number of live cells in the initial control sample, the *Salmonella typhimurium* solution concentration of live bacterial cells measured in colony forming units (CFU) is pre-counted on Nutrient Agar. Appropriate dilutions are made to transfer approximately 1,000 live CFU into each 50 mL control sample of carrot juice.

Test Samples: 50 mL of raw carrot juice containing 50 mg of lyophilized *Lactobacillus delbrueckii* subsp. *bulgaricus* (GLB 44) powder (powder concentration is 1×10$^9$ CFU/g) is contaminated with 1,000±100 live cells of *Salmonella typhimurium*. 5 identical test samples of 50 mL are prepared. The same method is used as in the control sample to ensure that 1,000±100 live CFU is placed in each 50 ml test sample.

To transfer the correct amount of GLB 44 powder and ensure that it is well mixed, the following method is used: Place 1 g of GLB 44 in 9 mL of sterile water at room temperature. Mix this solution for 3 to 5 minutes to ensure that it is homogeneous. Pipette 0.5 mL of the mixture and transfer to each 50 mL test sample.

The five test samples and the five control samples are placed in a refrigerated environment for 24 hours at 43° F. This replicates the manufacturing process for juice in which the vegetables are not cleaned properly and are contaminated with trace amounts of *Salmonella typhimurium*. In this process, the juice is produced and then cooled down for at least 24 hours prior to reaching the hands of the consumer.

After 24 hours at 43° F., the samples are placed in a chamber at a temperature of 98.6° F. for 48 hours. Since the transit time on average is longer than maximum pathogenic count value, it is therefore reasonable to leave the samples at 98.6° F. for 48 hours prior to making the bacterial count. The importance of this step is to see how the bacteria grows, and to determine whether GLB 44 has a pathogenic inhibitory effect once the bacteria is put into a body temperature environment, after 24 hours at refrigerating temperature.

After both periods have elapsed, each of the control samples and test samples are grown in Nutrient Agar (CM0003, Oxoid Limited, Basingstoke, Dartford) on which the GLB 44 does not grow but *Salmonella typhimurium* grows. The count of live bacteria is estimated by plating 10 fold dilutions in saline on Nutrient Agar and counting the colonies (CFU) in each dilution.

The same procedures are repeated for higher contaminant concentration of the *Salmonella typhimurium*, namely:

10,000 CFU/50 mL (200 CFU/mL)

100,000 CFU/50 mL (2,000 CFU/mL)

1,000,000 CFU/50 mL (20,000 CFU/mL)

10,000,000 CFU/50 mL (200,000 CFU/mL)

Results

The results for different concentrations of live bacteria after 48 hours with the solutions containing juice samples and the control sample are shown in TABLE 2. As shown in TABLE 2, for the control sample the growth of *S. typhimurium* exceeded 10 million CFU/mL while in the carrot juice that is populated with GLB 44 (1 million CFU/mL), there was no live pathogenic bacteria after 48 hours at 98.6° F. regardless of the initial pathogenic concentration, which varied from 20 CFU/mL to 200,000 CFU/mL.

TABLE 2

|  | Number of live bacteria in 48 hours at 98.6° F. (CFU/mL) with GLB 44 concentration 1 million CFU/mL | Number of live bacteria in 48 hours at 98.6° F. (CFU/mL) Control sample no LB present |
|---|---|---|
| *S. typhimurium* 2692 in carrot juice | | |
| 20 CFU/mL | no live pathogenic bacteria | greater than $0.10 \times 10^9$ |
| 200 CFU/mL | no live pathogenic bacteria | greater than $0.10 \times 10^9$ |
| 2,000 CFU/mL | no live pathogenic bacteria | greater than $0.10 \times 10^9$ |
| 20,000 CFU/mL | no live pathogenic bacteria | greater than $0.10 \times 10^9$ |
| 200,000 CFU/mL | no live pathogenic bacteria | greater than $0.10 \times 10^9$ |
| *E. coli* in carrot juice | | |
| 20 CFU/mL | no live pathogenic bacteria | greater than $0.12 \times 10^9$ |
| 200 CFU/mL | no live pathogenic bacteria | greater than $0.12 \times 10^9$ |
| 2,000 CFU/mL | no live pathogenic bacteria | greater than $0.12 \times 10^9$ |
| 20,000 CFU/mL | no live pathogenic bacteria | greater than $0.12 \times 10^9$ |
| 200,000 CFU/mL | no live pathogenic bacteria | greater than $0.12 \times 10^9$ |

As shown in Table 2, similar results were found with *E. coli*. In the control sample, the *E. coli* exceeded 120 million CFU/ml while in the carrot juice that is populated with GLB 44 (1 million CFU/mL), there were no live pathogenic bacteria after 48 hours at 98.6° F. regardless of the initial pathogenic concentration, which varied from 20 CFU/mL to 200,000 CFU/mL.

As shown by the results in TABLE 2, GLB 44 performs exceptionally well as a pathogenic inhibitor in vegan mediums. While other Lactic Acid Bacteria (LAB) have shown inhibitory effects against *Salmonella* and *E. coli*, no similar results on vegan foods have been observed. Table 3 summarizes scientific articles that explore the inhibitory effect of different LAB on *Salmonella*, *E. coli*, or both.

While many scientific studies exist about the inhibitory effects of the different Lactic Acid Bacteria, the present discovery that GLB 44 completely destroys *E. coli* and *Salmonella* contamination in vegan mediums is remarkable especially because GLB 44 is able to sustain itself in refrigerated temperatures for 24 hours before use. This unique property of GLB 44 is most likely due to its natural habitat being on the leaves of snowdrops which provides for its vitality in vegan-type mediums and its ability to sustain in low temperature because in its natural habitat the temperature falls below the freezing point.

Example 3

*Lactobacillus bulgaricus* Strain GLB 44 on *Salmonella* and *E. coli* in Vegan Juice 1. Test Materials
    (1) Lyophilized *Lactobacillus delbrueckii* subsp. *bulgaricus* GLB 44 powder (concentration=$1 \times 10^9$ CFU/g);
    (2) 2000 mL of organic carrot juice;
    (3) Nutrient Agar powder (CM0003, Oxoid Limited, Basingstoke, Dartford).
2. Bacterial Culture Preparation

*E. coli* (ATCC number: 25922) and *Salmonella enterica* subsp. *enterica* serovar *typhimurium* (ATCC number: 14028) were grown in Tryptic soy broth (TSB, Sigma Chemical Co., St. Louis, Mo.) medium at 37° C. with shaking for 16 hours.

Performed 10 fold dilutions from $10^{-1}$ to $10^{-8}$.

Plate 1000 μl of $10^{-6}$, $10^{-7}$ and $10^{-8}$ diluted samples on nutrient agar and incubate at 37° C. for 16 hours.

3. Preparation of the Organic Carrot Juice

Sterilize the juice for 10 seconds at 273° F. (134° C.). Cool down the juice to 43° F. (6° C.) in a refrigerator while keeping the sample completely sterile. Make 10 fold dilutions, and plate on TSA media at 37° C. for 16 hours to check that the carrot juice is truly sterile.

4. Inoculation of the Organic Carrot Juice with *E. coli* or *S. typhimurium*

Control Samples: The plate count showed that the initial culture for *E. coli* was $1.2 \times 10^9$ CFU/mL, and $1.0 \times 10^9$ CFU/mL for *S. typhimurium*. 10 fold dilutions were made separately from the initial cultures and 1,000±100 live cells were inoculated into the 10 tubes containing 50 mL organic carrot juice.

Test Samples: 50 mL of organic carrot juice that contains 50 mg of lyophilized *L. bulgaricus* powder (concentration=$1 \times 10^9$ CFU/g) is contaminated with 1,000 live cells of *E. coli* or *S. typhimurium*.

The following method was used to transfer the correct amount of GLB 44 powder: 1 g of *L. bulgaricus* was placed in 9 mL of sterile water at room temperature. the solution was mixed for 3 to 5 minutes to ensure homogeneity. With a pipette, 0.5 mL was removed and inserted into 5 tubes each for both 50 mL test samples.

5. Treatment
    (1) The 10 test samples and the 10 control samples were placed in a refrigerated environment held for 24 hours at 43° F.
    (2) After the end of the 24 hours at 43° F., the samples were put under a temperature of 98.6° F. for 48 hours.
6. Plate Count After both periods have elapsed, each of the control samples and test samples were serial diluted and plated out in Nutrient Agar.

Results

1. Test for *E. coli*

As shown in TABLE 3, no *E. coli* colony formation was detected on Nutrient Agar plates for all 5 samples that were inoculated with *L. bulgaricus*. Conversely, control samples that were not inoculated with *L. bulgaricus* showed the presence of $10^7$ CFU/mL *E. coli*.

TABLE 3

Bacterial plate count summary for E. coli

| Treatment | E. coli plate count (CFU/mL) |
|---|---|
| E. coli with Lb-1 | 0 |
| E. coli with Lb-2 | 0 |
| E. coli with Lb-3 | 0 |
| E. coli with Lb-4 | 0 |
| E. coli with Lb-5 | 0 |
| E. coli Ck-1 | $9.2 \times 10^7$ |
| E. coli Ck-2 | $3.8 \times 10^7$ |
| E. coli Ck-3 | $6.4 \times 10^7$ |
| E. coli Ck-4 | $4.5 \times 10^7$ |
| E. coli Ck-5 | $1.8 \times 10^7$ |

2. Test for *Salmonella typhimurium*

As shown in TABLE 4, no *Salmonella typhimurium* colony formation was detected on Nutrient Agar plates for all 5 samples that were inoculated with *L. bulgaricus*. Conversely, control samples that were not inoculated with *L. bulgaricus* showed the presence of $10^5$ CFU/mL *Salmonella typhimurium*.

TABLE 4

Bacterial plate count summary for Salmonella typhimurium

| Treatment | Salmonella plate count (cfu/ml) |
|---|---|
| Salmonella with Lb-1 | 0 |
| Salmonella with Lb-2 | 0 |
| Salmonella with Lb-3 | 0 |
| Salmonella with Lb-4 | 0 |
| Salmonella with Lb-5 | 0 |
| Salmonella Ck-1 | $1.6 \times 10^5$ |
| Salmonella Ck-2 | $8.2 \times 10^5$ |
| Salmonella Ck-3 | $3.7 \times 10^5$ |
| Salmonella Ck-4 | $3.2 \times 10^5$ |
| Salmonella Ck-5 | $1.2 \times 10^5$ |

Conclusion

The results from this experiment showed that *Lactobacillus bulgaricus* strain GLB 44 inhibited 100% of the *E. coli* and *Salmonella* contamination in vegan juice. It can also be concluded from the control samples, that without the presence of the *Lactobacillus bulgaricus* strain GLB 44, both *E. coli* and *Salmonella* thrive in vegan juice and small contamination of the food pathogens can reach high concentrations under the appropriate conditions that could cause a health hazard if consumed by humans.

Example 4

Comparison Data for 6 Different Strains of *Lactobacillus bulgaricus*

Test Materials

Lyophilized *Lactobacillus delbrueckii* subsp. *bulgaricus* for 6 different strains: LBB 5, LBB 26, LBB 37, GLB 44 (NBIMCC 8814), LBB 2, and LBB 14 (concentration=1×$10^6$ CFU/mL);

2000 mL of organic carrot juice; and

Nutrient Agar powder (CM0003, Oxoid Limited, Basingstoke, Dartford).

Bacterial Culture Preparation

Prepare and let sit overnight a culture of *E. coli* and *S. typhimurium* at 98.6° F. (37° C.) in Brain Hart Infusion or Nutrient Broth. Performed 10 fold dilutions in saline from $10^{-1}$ to $10^{-6}$ (for example, 0.5 mL of the culture in 4.5 mL of saline) using a separate tip for each dilution. Plate 100 µL of $10^{-4}$, $10^{-5}$, and $10^{-6}$ on nutrient agar and spread the samples on the agar surface. Count the number of bacterial colonies the next day. The observed count of live bacteria in the culture is approximately $10^{4.56}$ CFU/mL for *S. typhimurium* and $10^{4.69}$ CFU/mL for *E. coli*.

E. *Coli* Test Methodology

Test Samples: 50 mL of raw carrot juice containing 50 mg of the lyophilized *Lactobacillus delbrueckii* subsp. *bulgaricus* powder is contaminated with the live cells of *E. coli*. 3 identical test samples of 50 mL are prepared for each of the 6 strains.

The three test samples are placed in a refrigerated environment for 24 hours at 39.2° F. After 24 hours at 39.2° F., the samples are placed in a chamber at a temperature of 98.6° F. for 48 hours. After both periods have elapsed, the test samples are grown out in Nutrient Agar (CM0003, Oxoid Limited, Basingstoke, Dartford). The count of live bacteria is estimated by plating 10 fold dilutions in saline on Nutrient Agar and counting the colonies (CFU) in each dilution.

*Salmonella typhimurium* Test Methodology

Test Samples: 50 mL of raw carrot juice containing 50 mg of lyophilized *Lactobacillus delbrueckii* subsp. *bulgaricus* powder is contaminated with live cells of *Salmonella typhimurium*. 3 identical test samples of 50 mL are prepared.

The three test samples are placed in a refrigerated environment for 24 hours at 39.2° F. After 24 hours at 39.2° F., the samples are placed in a chamber at a temperature of 98.6° F. for 48 hours. After both periods have elapsed, the test samples are grown out in Nutrient Agar (CM0003, Oxoid Limited, Basingstoke, Dartford). The count of live bacteria is estimated by plating 10 fold dilutions in saline on Nutrient Agar and counting the colonies (CFU) in each dilution.

TABLE 5

Inhibition of S. typhimurium by Lactobacillus delbrueckii subsp. bulgaricus

| Strain | LBB 5 | LBB 26 | LBB 37 | GLB 44 | LBB 2 | LBB 14 |
|---|---|---|---|---|---|---|
| NBIMCC Code | NBIMCC 273 | NBIMCC 285 | NBIMCC 286 | NBIMCC 8814 | NBIMCC 1273 | NBIMCC 1132 |
| Initial Contamination of S. typhimurium | $10^{4.56}$ CFU/mL | $10^{4.56}$ CFU/mL | $10^{4.56}$ CFU/mL | $10^{4.56}$ CFU/mL | $10^{4.56}$ CFU/mL | $10^{4.56}$ CFU/mL |
| Initial Concentration of L. Bulgaricus | $10^{6.00}$ CFU/mL | $10^{6.00}$ CFU/mL | $10^{6.00}$ CFU/mL | $10^{6.00}$ CFU/mL | $10^{6.00}$ CFU/mL | $10^{6.00}$ CFU/mL |
| Duration of sample exposure to 4° C. (39.2° F.) | 24 hours | 24 hours | 24 hours | 24 hours | 24 hours | 24 hours |
| Duration of sample exposure to 37° C. (98.6° F.) | 48 hours | 48 hours | 48 hours | 48 hours | 48 hours | 48 hours |

TABLE 5-continued

Inhibition of S. typhimurium by Lactobacillus delbrueckii subsp. bulgaricus

| Strain | LBB 5 | LBB 26 | LBB 37 | GLB 44 | LBB 2 | LBB 14 |
|---|---|---|---|---|---|---|
| Trial 1 | | | | | | |
| Final Contamination S. typhimurium | $10^{3.15}$ CFU/mL | $10^{3.36}$ CFU/mL | $10^{2.68}$ CFU/mL | 0.00 | $10^{2.90}$ CFU/mL | $10^{3.98}$ CFU/mL |
| Percent Inhibition | 96.1% | 93.7% | 98.7% | 100.0% | 97.8% | 73.8% |
| Trial 2 | | | | | | |
| Final Contamination S. typhimurium | $10^{3.54}$ CFU/mL | $10^{3.40}$ CFU/mL | $10^{2.89}$ CFU/mL | 0.00 | $10^{2.48}$ CFU/mL | $10^{3.48}$ CFU/mL |
| Percent Inhibition | 90.5% | 93.1% | 97.9% | 100.0% | 99.2% | 91.7% |
| Trial 3 | | | | | | |
| Final Contamination S. typhimurium | $10^{2.45}$ CFU/mL | $10^{3.49}$ CFU/mL | $10^{3.13}$ CFU/mL | 0.00 | $10^{2.38}$ CFU/mL | $10^{4.19}$ CFU/mL |
| Percent Inhibition | 99.2% | 91.5% | 96.3% | 100.0% | 99.3% | 57.6% |
| Average Inhibition (over 3 trials) | 95.3% | 92.8% | 97.6% | 100.0% | 98.8% | 74.4% |

TABLE 6

Inhibition of E. Coli by Lactobacillus delbruecki subsp. bulgaricus

| Strain | LBB 5 | LBB 26 | LBB 37 | GLB 44 | LBB 2 | LBB 14 |
|---|---|---|---|---|---|---|
| NBIMCC Code | NBIMCC 273 | NBIMCC 285 | NBIMCC 286 | NBIMCC 8814 | NBIMCC 1273 | NBIMCC 1132 |
| Initial Contamination E. coli | $10^{4.69}$ CFU/mL | $10^{4.69}$ CFU/mL | $10^{4.69}$ CFU/mL | $10^{4.69}$ CFU/mL | $10^{4.69}$ CFU/mL | $10^{4.69}$ CFU/mL |
| Initial Concentration of L. bulgaricus | $10^{6.00}$ CFU/mL | $10^{6.00}$ CFU/mL | $10^{6.00}$ CFU/mL | $10^{6.00}$ CFU/mL | $10^{6.00}$ CFU/mL | $10^{6.00}$ CFU/mL |
| Duration of sample exposure to 4° C. (39.2° F.) | 24 hours | 24 hours | 24 hours | 24 hours | 24 hours | 24 hours |
| Duration of sample exposure to 37° C. (98.6° F.) (in $10^{Coefficient}$ CFU/mL) | 48 hours | 48 hours | 48 hours | 48 hours | 48 hours | 48 hours |
| Trial 1 | | | | | | |
| Final Contamination E. coli | $10^{3.54}$ CFU/mL | $10^{3.81}$ CFU/mL | $10^{2.98}$ CFU/mL | 0.00 | $10^{3.10}$ CFU/mL | $10^{4.14}$ CFU/mL |
| Percent Inhibition | 93.0% | 87.0% | 98.1% | 100.0% | 97.5% | 72.1% |
| Trial 2 | | | | | | |
| Final Contamination E. coli | $10^{3.45}$ CFU/mL | $10^{3.85}$ CFU/mL | $10^{3.11}$ CFU/mL | 0.00 | $10^{3.21}$ CFU/mL | $10^{3.76}$ CFU/mL |
| Percent Inhibition | 94.3% | 85.7% | 97.4% | 100.0% | 96.7% | 88.4% |
| Trial 3 | | | | | | |
| Final Contamination E. coli | $10^{3.13}$ CFU/mL | $10^{3.88}$ CFU/mL | $10^{2.78}$ CFU/mL | 0.00 | $10^{3.60}$ CFU/mL | $10^{3.99}$ CFU/mL |
| Percent Inhibition | 97.3% | 84.7% | 98.8% | 100.0% | 92.0% | 80.3% |
| Average Inhibition (over 3 trials) | 94.9% | 85.8% | 98.1% | 100.0% | 95.4% | 80.2% |

As disclosed in TABLE 5 and TABLE 6, inoculation with GLB 44 inhibited 100% of both *S. typhimurium* and *E. coli*. Conversely, inoculation with other strains of *Lactobacillus delbrueckii* subsp. *bulgaricus* showed an inhibition of between 74.4-98.8% for *S. typhimurium* and between 80.2-98.1% for *E. coli*. Although this difference does not appear to be large, it is nonetheless significant when one considers that even a few live bacteria could increase to very large populations very quickly.

Example 5

Pathogen Inhibitory Effect of GLB 44 Against *E. coli*

Test Goal

This example was designed to determine whether *Lactobacillus delbrueckii* subsp. *bulgaricus* (GLB 44) inhibits the growth of *Escherichia coli* (*E. coli*) in vegetable juice.

Test Materials

Lyophilized *Lactobacillus delbrueckii* subsp. *bulgaricus* GLB 44 powder (concentration=$1\times10^9$ CFU/g);

Vegetable juice (3 bottles of Juice Press Organic Complete Source (17 fluid ounces each))—Juice Press Organic Complete Source is a mixed vegetable juice that includes celery, spinach, and parsley;

Tryptic Soy Agar Plates (TSA); and

*Esherichia coli* (*E. coli*)—ATCC 25922.

Bacterial Inoculum

*E. Coli*

A previously prepared frozen tube of *E. coli* stock culture was used. The bacterial concentration was $1.32\times10^9$ CFU/mL.

For the *E. coli* and Test Samples: The frozen tube containing *E. coli* was removed from the freezer and allowed to thaw at room temperature. The bacteria were diluted (1:10000) in sterile phosphate buffered saline to achieve a concentration of approximately $1\times10^5$ CFU/mL. 50 µL of this dilution was added to each of the control and test samples to achieve a concentration of approximately $1\times10^2$ CFU/mL.

*Lactobacillus delbrueckii* subsp. *bulgaricus* (GLB 44)

2 grams of *Lactobacillus delbrueckii* subsp. *bulgaricus* (GLB 44) was added to 18 mL of sterile water at room temperature. The solution was mixed using a vortex for 5 minutes to ensure the homogeneity of the mixture. 0.5 mL of the prepared solution was added to each of the test samples.

Test Procedure

The following test samples were prepared for the *E. coli*:

Control Samples: 5 bottles containing 50 mL each of the vegetable juice.

Test Samples: 5 bottles containing 50 mL each of boiled vegetable juice plus *Lactobacillus delbrueckii* subsp. *bulgaricus* (GLB 44)

*E. coli* was added to the control and test samples as described above. All of the samples were stored in a refrigerator (4° C.) for 24 hours. Following refrigeration, the bacterial concentration for each sample was determined. Serial 10 fold dilutions were made in phosphate buffered saline. A 0.1 mL aliquot of each dilution was plated onto TSA. The agar plates were incubated at 37° C. for 24 hours before enumeration—all counts were recorded as CFU/mL. All test and control samples were then placed at 37° C. for 48 hours. Following incubation, the bacterial concentration for each sample was determined as previously described.

Results

The results for samples of *E. coli* after 48 hours with the solutions containing test and control sample are shown in TABLE 7. As shown in TABLE 7, for the control sample the growth of *E. coli* exceeded 60,000 CFU/mL while in the vegetable juice that was populated with GLB 44, there was no *E. coli* after 48 hours at 37° C.

TABLE 7

| Vegetable juice | Number of *E. coli* after 48 hours at 37° C. (CFU/mL) Control sample no GLB 44 present | Number of *E. coli* after 48 hours at 37° C. (CFU/mL) Test sample with GLB 44 present |
| --- | --- | --- |
| 1 | 87,096 | 0 |
| 2 | 64,565 | 0 |
| 3 | 58,884 | 0 |
| 4 | 30,903 | 0 |
| 5 | 60,256 | 0 |
| Sample Average | 60,341 | 0 |
| % Inhibition - 48 hours pathogenic levels by *L. bulgicarus* | | 100.00% |

In TABLE 8, scientific articles are provided that have studied the inhibitory effects of Lactic Acid Bacteria and in these studies while showing partial inhibition, have not shown complete pathogenic destruction. It is well-known that the different strains of bacteria even from the same subspecies can vary substantially in their performance. This is attributable to the fact that the natural habitat of those species varies the similar genetic composition. For example, as shown in Table 8, a study with a different strain of *Lactobacillus delbrueckii*, *Lactobacillus delbrueckii* subsp. *bulgaricus* strain DSM 20081, shows that the inhibitory performance with this strain only reached 77% again *E. coli*.

Thus, due to its adaptation to its natural habitat, GLB 44 has the unique quality of being very vital in plant medium—able to survive in refrigerated temperature and able to achieve unprecedented complete inhibitory characteristics towards *E. coli* and *S. typhimurium*.

TABLE 8

Comparative Studies Involving LAB Inhibitory Effect on *Salmonella* and *E. coli*

| Scientific Study | Bacterial Cultures Involved and Determination of Inhibition | Result Quotation |
| --- | --- | --- |
| "Antagonistic Activity Exerted In Vitro and In Vivo by *Lactobacillus casei* (Strain GG) against *Salmonella typhimurium* C5 Infection," *Applied and Environmental Microbiology* 63: 513-518 (2007). | *Lactobacillus casei* *Salmonella typhimuirum*: Some conditional inhibitory effect - no absolute inhibition. | "the invasion of the Caco-2 cells by *S. typhimurium* C5 is strongly reduced when the pathogen has been in contact for 1 h with the culture . . . When both the spent culture supernatant and the culture of *L. casei* GG were neutralized at pH 7, the number of *Salmonella* |

TABLE 8-continued

Comparative Studies Involving LAB Inhibitory Effect on *Salmonella* and *E. coli*

| Scientific Study | Bacterial Cultures Involved and Determination of Inhibition | Result Quotation |
|---|---|---|
| | | organisms invading cells was not different from that obtained with *Salmonella* organisms treated with neutralized MRS broth or with PBS." |
| "In vitro evaluation of anti-infective activity of a *Lactobacillus plantarum* strain against *Salmonella enterica* serovar *Enteritidis*," *Gut Pathogens* 5: 11 (2013). | *Lactobacillus plantarum* *Salmonella enterica* serovar *Enteritidis* Evident inhibitory effect but still limited to 80% reduction. | "Further, the anti-infective characteristics of KSBT 56 strain was validated by gentamicin protection assay which revealed 80% reduction in the invasion of *Salmonella Enteritidis*" |
| "pH-, Lactic Acid-, and Non-Lactic Acid-Dependent Activities of Probiotic Lactobacilli against *Salmonella enterica* Serovar *Typhimurium*," *Applied and Environmental Microbiology* 71: 6008-6013 (2005). | *Lactobacillus johnsonii* *Lactobacillus rhamnosu* *Lactobacillus casei* *Salmonella typhimuirum* Inhibitory effect present on the growth of the pathogen without complete destruction. | "A decrease of 3.5 logs in viable serovar *Typhimurium* SL1344 was observed." |
| "Inhibition of *Escherichia coli* O157:h7 by *Lactobacillus Acidophilus* isolated from calves" | *Lactobacillus Acidophilus*, *E. coli* Variable inhibitory effect present on the growth of the pathogen without complete destruction reaching up to 96%. | "Data obtained from the initial experiments revealed significant variation in the inhibitory action (% inhibition) among strains of calf *L. acidophilus* towards *E. coli* O157:H7 and *S. aureus* cultures" |
| "In vitro anti-bacterial and anti-adherence effects of *Lactobacillus delbrueckii* subsp *bulgaricus* on *Escherichia coli*," *Res. Pharm. Sci.* 8: 260-268 (2013) | *Lactobacillus delbrueckii* subsp. *bulgaricus* strain DSM 20081, *E. coli* Inhibitory effect present on the growth of the pathogen without complete destruction. | "When two bacteria added simultaneously (competitive inhibition) degree of inhibition of *E. coli* binding by *L. delbrueckii* was 77%." |

Having now fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed is:

1. A method of treating vegetable juice potentially contaminated with *E. coli*, *Salmonella*, or *Listeria monocytogenes*, comprising treating the vegetable juice with a composition comprising from $0.5 \times 10^6$ to $5 \times 10^6$ CFU/mL lyophilized *Lactobacilli* and a plant-based growth medium, wherein the *Lactobacilli* is *Lactobacillus bulgaricus* strain GLB 44, deposited at the National Bank for Industrial Microorganisms and Cell Cultures, Sofia, Bulgaria, under Accession Number 8814, wherein the composition is substantially free of animal products, and wherein the composition is stored at a temperature of less than 26° C.

2. The method of claim 1, wherein the composition contains no animal products.

3. The composition of claim 1, wherein the *Lactobacilli* is combined with or applied to the vegetable juice in the form of a powder.

4. The method of claim 1, wherein the *Lactobacilli* is combined with or applied to the vegetable juice in the form of a solution or suspension.

5. The method of claim 1, wherein the vegetable juice is carrot juice.

6. A method of reducing *E. coli*, *Salmonella*, or *Listeria monocytogenes* contamination of a vegetable juice, comprising combining with or applying to the vegetable juice a composition comprising from $0.5 \times 10^6$ to $5 \times 10^6$ CFU/mL lyophilized *Lactobacilli*, wherein the composition is substantially free of animal products, and wherein the *Lactobacilli* is *Lactobacillus bulgaricus* strain GLB 44, deposited at the National Bank for Industrial Microorganisms and Cell Cultures, Sofia, Bulgaria, under Accession Number 8814, and wherein the composition is stored at a temperature of less than 26° C.

7. The method of claim 6, wherein the composition contains no animal products.

8. The method of claim 6, wherein the *Lactobacilli* is combined with or applied to the vegetable juice in the form of a powder.

9. The method of claim 6, wherein the *Lactobacilli* is combined with or applied to the vegetable juice in the form of a solution or suspension.

10. The method of claim 6, wherein the vegetable juice is carrot juice.

11. The method of claim 1, wherein after treating the vegetable juice with the composition, the vegetable juice is stored at a temperature between 35° F. and 50° F.

12. The method of claim 6, wherein after combining or applying the composition to the vegetable juice, the vegetable juice is stored at a temperature between 35° F. and 50° F.

* * * * *